United States Patent [19]
Takahashi et al.

[11] Patent Number: 5,253,647
[45] Date of Patent: Oct. 19, 1993

[54] INSERTION POSITION AND ORIENTATION STATE PICKUP FOR ENDOSCOPE

[75] Inventors: Yutaka Takahashi, Hachioji; Yoshikatsu Nagayama, Sagamihara; Hiroki Hibino, Hachioji; Katsunori Sakiyama, Akigawa; Yoshihito Shimizu, Hachioji; Sakae Takehana, Machida; Yoshinao Ōaki; Koji Koda, both of Hachioji; Yoshinobu Soeda, Fukuoka; Masato Toda, Hachioji; Toshiaki Noguchi, Tachikawa; Yuichi Yamada, Tokyo; Akira Ōsawa, Yokohama, all of Japan

[73] Assignee: Olympus Optical Co., Ltd., Tokyo, Japan

[21] Appl. No.: 684,405

[22] Filed: Apr. 12, 1991

[30] Foreign Application Priority Data

Apr. 13, 1990 [JP] Japan ................................. 2-98521
Dec. 12, 1990 [JP] Japan ................................ 2-401686

[51] Int. Cl.$^5$ ............................................. A61B 5/05
[52] U.S. Cl. ...................................... 128/653.1; 128/4
[58] Field of Search ................. 128/4, 653.1–653.2, 128/0.5; 600/7, 10–14

[56] References Cited

U.S. PATENT DOCUMENTS

| | | | |
|---|---|---|---|
| 4,173,228 | 11/1979 | Van Steerwyck et al. ...... | 128/653.1 |
| 4,176,662 | 12/1979 | Frazer ...................................... | 128/6 |
| 4,416,289 | 11/1983 | Bresler ............................... | 600/11 X |
| 4,431,005 | 2/1984 | McCormick ......................... | 128/656 |
| 4,572,198 | 2/1986 | Codrington ...................... | 128/653.2 |
| 4,810,875 | 3/1989 | Wyatt ................................ | 128/664 X |
| 4,821,731 | 4/1984 | Martinelli et al. ............ | 128/653.1 X |
| 4,905,698 | 3/1990 | Strohl, Jr. et al. ................ | 600/13 X |
| 5,042,486 | 8/1991 | Pfeiler et al. ...................... | 128/653.1 |
| 5,057,095 | 10/1991 | Fabian ............................... | 600/12 X |
| 5,099,845 | 3/1992 | Besz et al. .......................... | 128/653.1 |

FOREIGN PATENT DOCUMENTS 0000594  8/1979  PCT Int'l Appl. ................. 128/664

*Primary Examiner*—Francis Jaworski
*Attorney, Agent, or Firm*—Armstrong, Westerman, Hattori, McLeland & Naughton

[57] ABSTRACT

A position and orientation state pickup is designed to detect the position and orientation state of an endoscope inserted into a living body without any adverse effect on the living body, which is often observed in X-ray analysis. The position and orientation state pickup, generating an electro-magnetic field with frequency at least lower than the visible ray range toward the body from outside; detects influence of the endoscope inserted into the body on two-dimensional energy distribution of the electro-magnetic field generated toward the body; and show the position and orientation state of the endoscope from the detection results.

18 Claims, 18 Drawing Sheets

FIG. 4
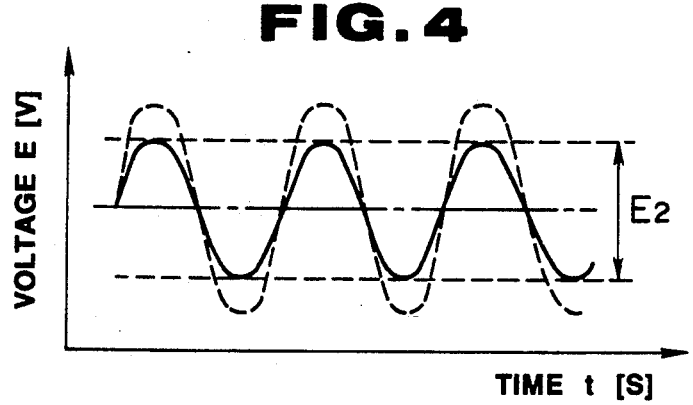
FIG. 5
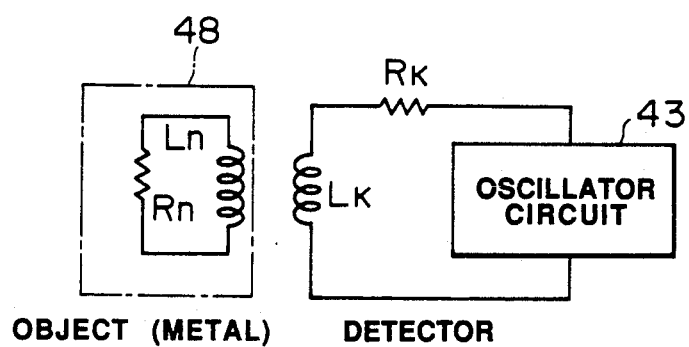
FIG. 6(a) FIG. 6(b) FIG. 6(c)
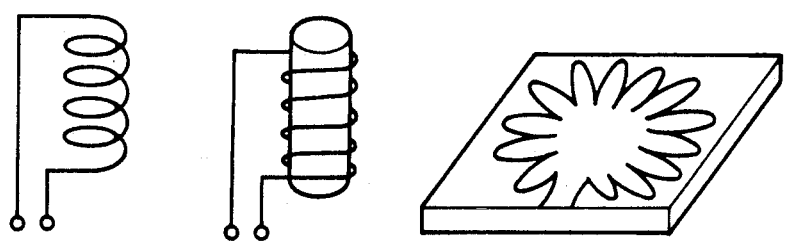

FIG. 24 B
FIG. 24 A
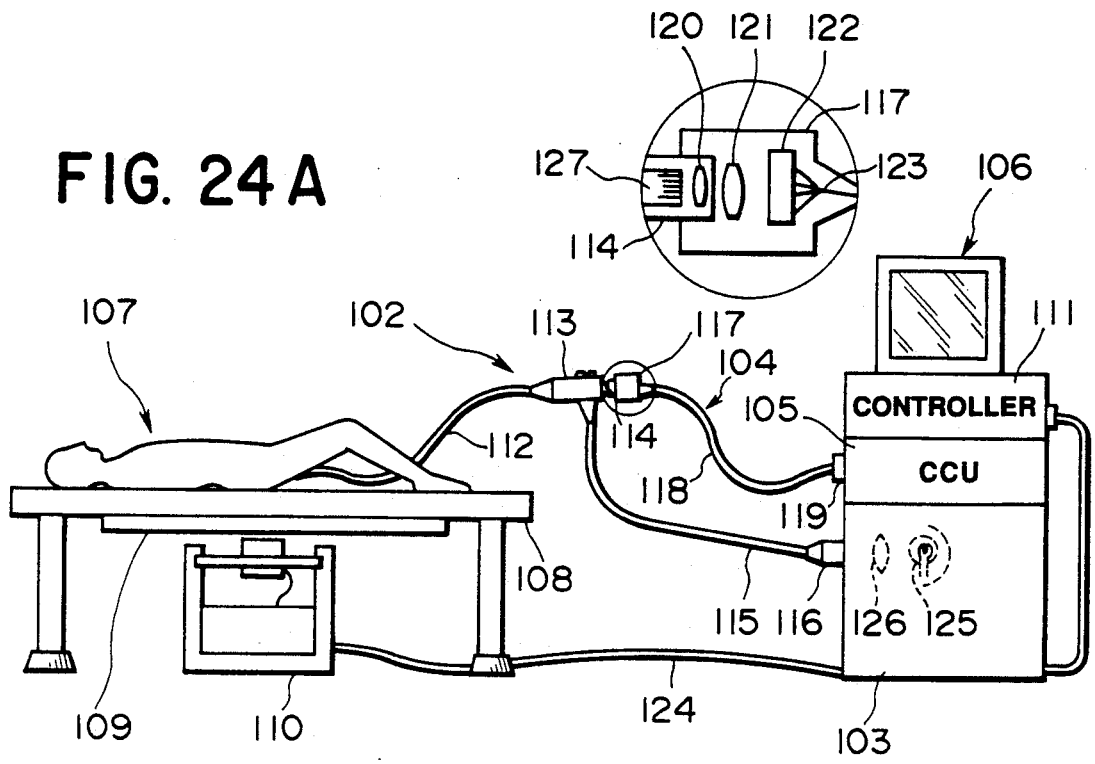
FIG. 25
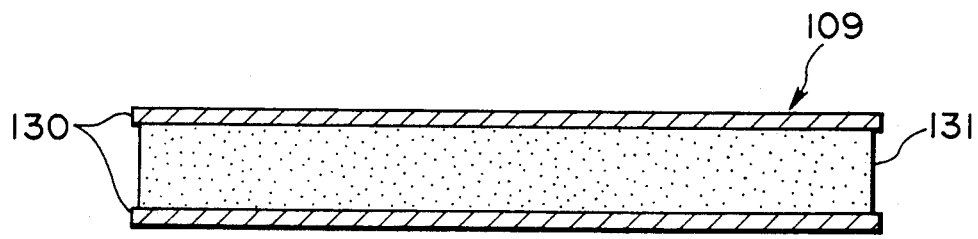

INSERTION POSITION AND ORIENTATION STATE PICKUP FOR ENDOSCOPE

BACKGROUND OF THE INVENTION

1. Field of the Invention

This invention relates to a pickup to detect an insertion position and orientation of the insertion unit of the endoscope into body to be tested.

2. Description of Related Art

In general, an endoscope apparatus is designed to insert a thin, flexible insertion unit into a part to be inspected in a body cavity and to observe or treat, if necessary, such inspected part. Since the body cavity, such as the small and large intestines, is typically of a winding shape, the position and orientation of the inserted endoscope insertion unit is not readily known to the operator.

Traditionally, an X ray is irradiated to the inspected part with the endoscope insertion unit inserted from outside of the body to check the insertion state, such as insertion position and orientation of the insertion unit in the body cavity.

Such X ray, however, is not completely harmless to the body and restricts irradiation parts, thus not always being suitable as a detection method for insertion state of the endoscope insertion unit.

While a pickup, as set forth in the U.S. Pat. No. 4,176,662, to detect the position of the tip of an endoscope or a catheter to be inserted into body cavities is available at present, the pickup has no capability of detecting the orientation and state of the endoscope inserted in winding body cavity.

SUMMARY OF THE INVENTION

It is a first object of the present invention to provide a pickup to detect an insertion position and orientation of an endoscope inserted into a body cavity without producing adverse effects on the body as given by X-ray radiation.

· It is a second object of the present invention to provide a pickup irradiating the detecting electro-magnetic energy to a relatively wide range. The pickup, using electro-magnetic energy with low frequency, is designed to minimize any adverse effects on the human body, while ensuring detection of the insertion position and orientation of the endoscope inserted into a body cavity.

It is a further object of the present invention to provide a pickup to detect an insertion position and orientation of a general, existing endoscope inserted into a body cavity without attaching irradiation means of electro-magnetic energy and detection means on the endoscope, and without adding an irradiation or detection function to the endoscope.

In brief explanation, the present invention is a pickup to detect the insertion position and orientation of an endoscope inserted into a body cavity of an organism, comprising a means to form an electro-magnetic field with a frequency lower than the visible radiation range from outside of the body and a means for detecting two-dimensional energy distribution in such electro-magnetic field influenced by the endoscope inserted into the body cavity.

These and other objects, as well as advantages of the present invention, will become clear by the following description of the preferred embodiment of the present invention with reference to the accompanying drawings.

BRIEF DESCRIPTION OF THE DRAWINGS

FIGS. 1 to 8 relate to the first embodiment of the present invention.

FIG. 1 is a schematic view of the endoscope and the insertion-state pickup for the endoscope.

FIG. 2 is an oscillator circuit diagram of FIG. 1.

FIG. 3 is a wave form graph explaining movement of the oscillator circuit in FIG. 2.

FIG. 4 is a wave form graph explaining movement of the oscillator circuit in FIG. 2.

FIG. 5 is an explanatory diagram showing the movement principle of the insertion-state pickup for the endoscope.

FIG. 6 is an explanatory diagram showing several embodiments of pickup coils.

FIG. 7 is a wave form graph showing the resonance characteristic of the oscillator circuit.

FIG. 8 is an explanatory diagram showing indication examples by the insertion-state pickup for the endoscope.

FIG. 15 is an operational diagram of the apparatus shown in FIG. 1.

FIG. 16 is a schematic diagram showing the layout of the light-emitting means and light detection means.

FIG. 17 is a perspective view of the light-emitting means and light detection means.

FIG. 18 is a schematic diagram of the apparatus shown in FIG. 3.

FIG. 19 is an explanatory diagram showing the state of the endoscope inserted in the living body.

FIG. 20 is an explanatory diagram showing indication examples of the insertion-state pickup for the endoscope.

FIG. 22 is a schematic diagram of the insertion-state pickup for the endoscope.

FIG. 23 is a schematic diagram showing the scanner of the apparatus shown in FIG. 22.

FIGS. 24 to 26 relate to the eighth embodiment of the present invention.

FIG. 24 is a schematic diagram showing the insertion-state pickup for the endoscope.

FIG. 25 is a sectional view of the magnetic detection means.

FIG. 26 is an explanatory diagram showing detection condition by the magnetic detection means.

FIG. 27 is a schematic diagram showing the insertion-state pickup for the endoscope.

FIG. 28 is an explanatory diagram showing the magnetic detection means.

DESCRIPTION OF THE PREFERRED EMBODIMENTS

FIGS. 1 to 8 relate to a device to detect the insertion state of the endoscope with the aid of magnetic means.

The insertion-state pickup for the endoscope in this embodiment is designed to detect the insertion position and orientation the endoscope by detecting the change caused by the endoscope in the magnetic field generated by a magnetic-field generating means.

Figure 1:
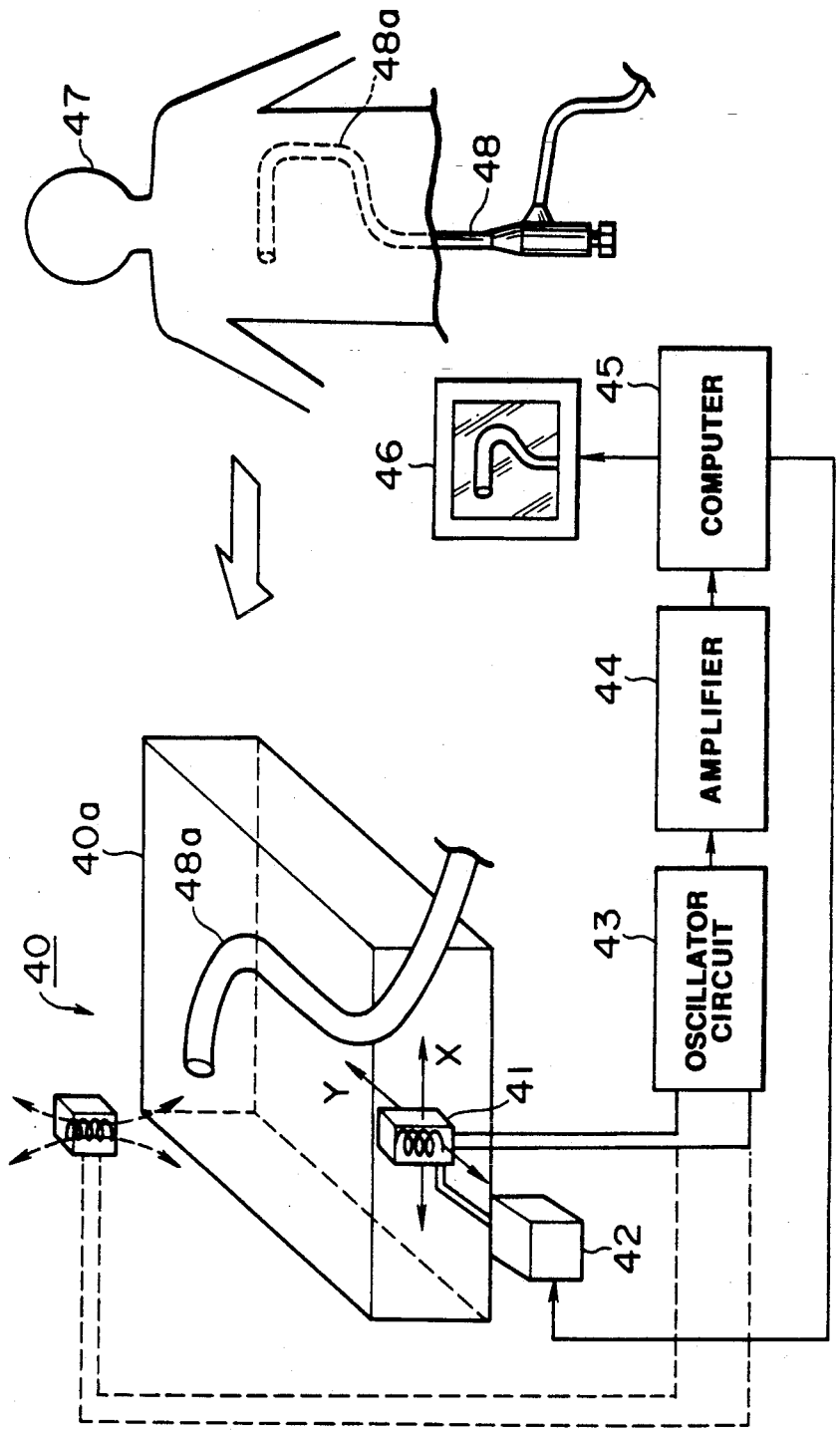

An insertion-state pickup for the endoscope 40 shown in FIG. 1, located inside a bed 40a, comprises a pickup coil 41 as a magnetic-field generating means movable in the X and Y directions in the figure; a scanner controller 42 for moving the pickup coil 41 for scanning; an oscillator circuit 43 serving as an oscillation means to allow the pickup coil 41 to generate the alternating magnetic force and also as a detection means to detect a change in alternating magnetic field generated by the pickup coil 41; an amplifier 44 amplifying the magnetic change generated by the pickup coil 41 and detected by the oscillation circuit 43; a computer 45 for analyzing and processing signals output by the amplifier 44 and controlling the scanning by the pickup coil 41 via the scanner controller 42; and a monitor 46 for displaying the position and orientation state of an endoscope 55 by using standard image signals output by the computer 45. A body to be tested 47, laid on the bed 40a, receives insertion of an insertion unit 48a of an endoscope 48. The position and orientation state pickup for endoscope 40 indicates the position and insertion state of the insertion unit 48a.

The pickup coil 41, as shown in FIG. 1, can be installed on the tested body 47 on the bed 40a for scanning. The dotted lines in FIG. 1 show connection of the pickup coil 41 and the oscillator circuit 43 in that case.

Figure 2:
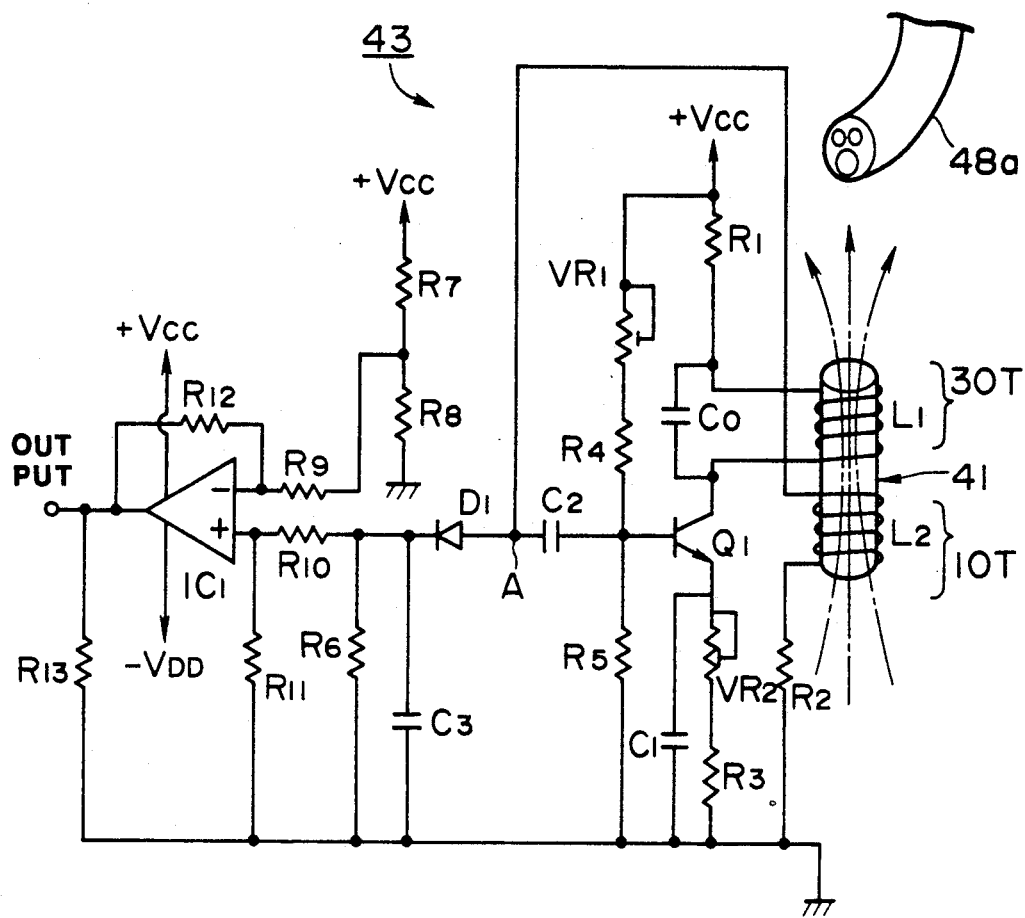

FIG. 2 shows actual wiring configuration of the oscillator circuit 43. The oscillator circuit, which is a high-frequency oscillator circuit of resonance type, comprises a self-exciting LC oscillator circuit oscillating in combination with the pickup coil 41 and generating alternating signals; a smoothing circuit for smoothing signals which fluctuate according to the resonance characteristic of the capacitor of the LC oscillator circuit and the pickup coil 41; and a differential amplifier circuit for outputting a signal when a signal smoothed by the smoothing circuit exceeds the standard signal. The LC oscillator circuit, incorporating a transistor Q1, resistors R1 to R5, variable resistors VR1 and VR2, an oscillation capacitor C0, and capacitors C1 and C2, is combined with the pickup coil 41. The smoothing circuit comprises a diode D1, a capacitor C3, and a resistor R6. The differential amplifier circuit comprises resistors R7 and R8 for generating standard voltage E0 by dividing the power supply +VCC, resistors R9 to R13, and a differential amplifier IC1 connecting the power supply +VCC with the power supply −VCC. The standard voltage E0 at the contact of the resistors R7 and R8 is set equivalent to the voltage at the contact (A in the figure) of the capacitor C2 and the diode D1 without the detected object such as the insertion unit 48 of the endoscope. The pickup coil 41 is constructed by winding the first coil L1 and the second coil L2 on the core material. The turn ratio of the first coil L1 and the second coil L2 is set at 3 to 1, for example. The second coil L2 is wound so that the output of the second coil L2 is in the same phase with the collector output of the transistor Q1. Therefore positive feedback is applied to the transistor Q1. The oscillation frequency f0 of the oscillator circuit 43 is determined by the equation below.

$$f0 = 1/(2\pi \sqrt{(L1 \cdot C0)}) \quad (1)$$

The detection principle of the position and orientation state pickup 40 of the endoscope is explained below by referring to FIG. 5. When the detected object, metal insertion unit 48a of the endoscope approaches the pickup coil 41, the pickup coil 41 receives generated magnetic lines of force, an eddy current is generated in the insertion unit 48a of the endoscope due to electromagnetic induction. The insertion unit 48a of the endoscope (metal part), as shown in FIG. 5, can be equivalently expressed with the self-inductance Ln and resistor Rn. When the self-inductance of the pickup coil 41 is set as Lk, the internal resistance as Rk, and the mutual inductance between the pickup coil 41 and the insertion unit 48a of the endoscope as M, the impedance Z from the pickup coil 41 side is obtained by the equation:

$$Z=[Rn\{\omega M/(Rn+\omega Ln)\}^2+j\omega LK+\{\omega M/(Rn+\omega Ln)\}^2]$$

Figure 11:
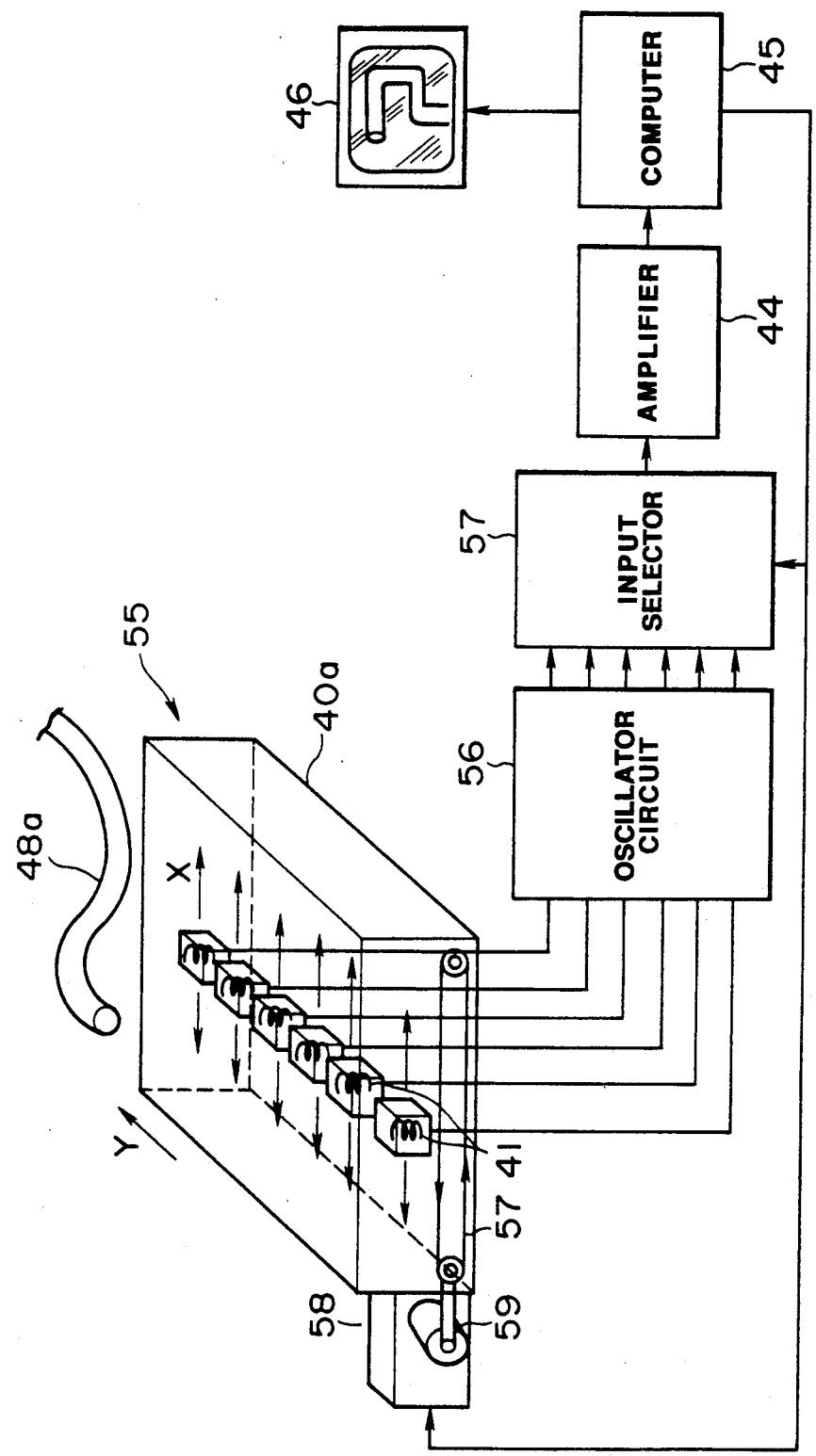
FIG. 11 is a schematic diagram of the insertion-state pickup for the endoscope relating to the second embodiment of the present invention.

The resistance of the pickup coil 41 increases by $\{\omega M/(Rn+\omega Ln)^2\}3$, and the quality factor Q of the circuit decreases. As the insertion unit 48a of the endoscope goes away, the Q increases. The oscillator circuit 43 can detect the insertion unit 48a of the endoscope by sensing a change in high-frequency current or volatage along the change of Q in the resonant LC oscillator circuit. As shown in FIG. 11, the insertion-state pickup 40 receives detection output of each coordinate (x, y) by scanning the pickup coil 41 in the X and Y directions and obtains the three-dimensional position and state of the insertion unit 48a of the endoscope by using the detection output in the Z axis. The said quality factor Q is detailed below. In the resonant LC oscillator circuit having the coil and the capacitor in parallel connection, Q is described by:

$$Q=\tfrac{1}{2}\pi f0 \cdot C \cdot Rs = 2\pi f0 \cdot L/Rs.$$

Here f0 is the resonant frequency and Rs is the direct current resistance of the coil.

Figure 3:
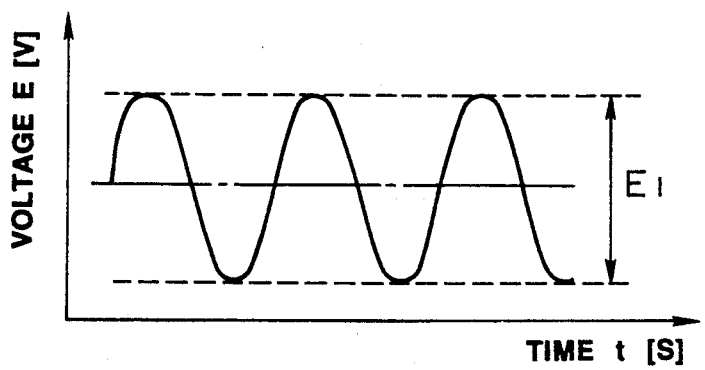
Figure 7:
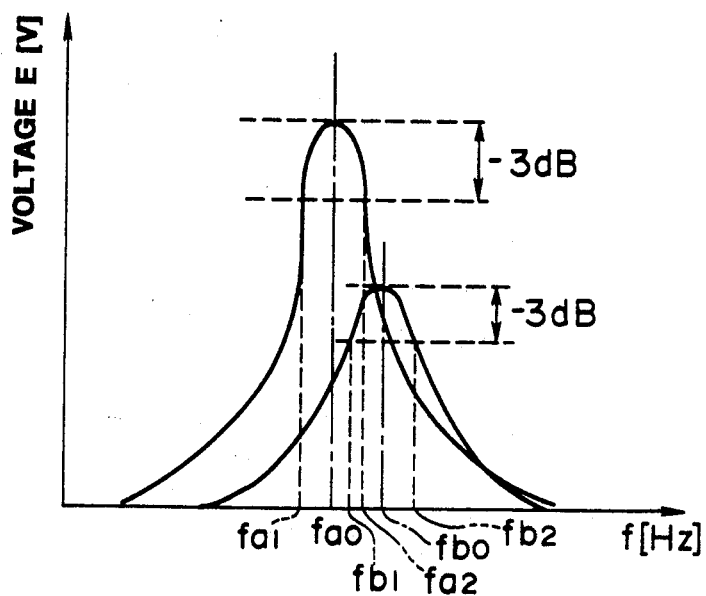

Position detection by the oscillator circuit 43 shown in FIG. 2 is detailed below. This self-exciting oscillator circuit oscillates with power turned on, and high-frequency alternating current flows through the pickup coil 41, which in turn causes an alternating magnetic field. When no insertion unit 48a of the endoscope is located in the vicinity, the value Q of the circuit remains unchanged. As shown in FIG. 7, oscillation starts and the maximum output is obtained at the frequency f0 obtained by the equation (1). The feedback voltage E at the point A in FIG. 2 becomes the maximum E1, as shown in FIG. 3. When fa1 and fa2 represent frequencies having the reduced voltage (or current) value of −3dB from the voltage (or current) value of the resonant frequency fa0, as shown in FIG. 7, the value Q of the circuit, has this relation $$Q = fa0/B.$$

Here B is the half band width, which is given by $$B = fa2 - fa1.$$

FIG. 7 also shows an example with low Q property, dull rise around the resonant frequency, and low detecting sensitivity at the circuit frequency fb0.

The insertion unit 48a of the endoscope, approaching the pickup coil 41, disturbs the magnetic field of the pickup coil 41 and lowers the value Q of the circuit by the change in impedance as mentioned earlier. The feedback current through the second coil L2 decreases, and the feedback voltage E at the point A in FIG. 2 decreases to the voltage E2 as shown in FIG. 4.

Figure 8:
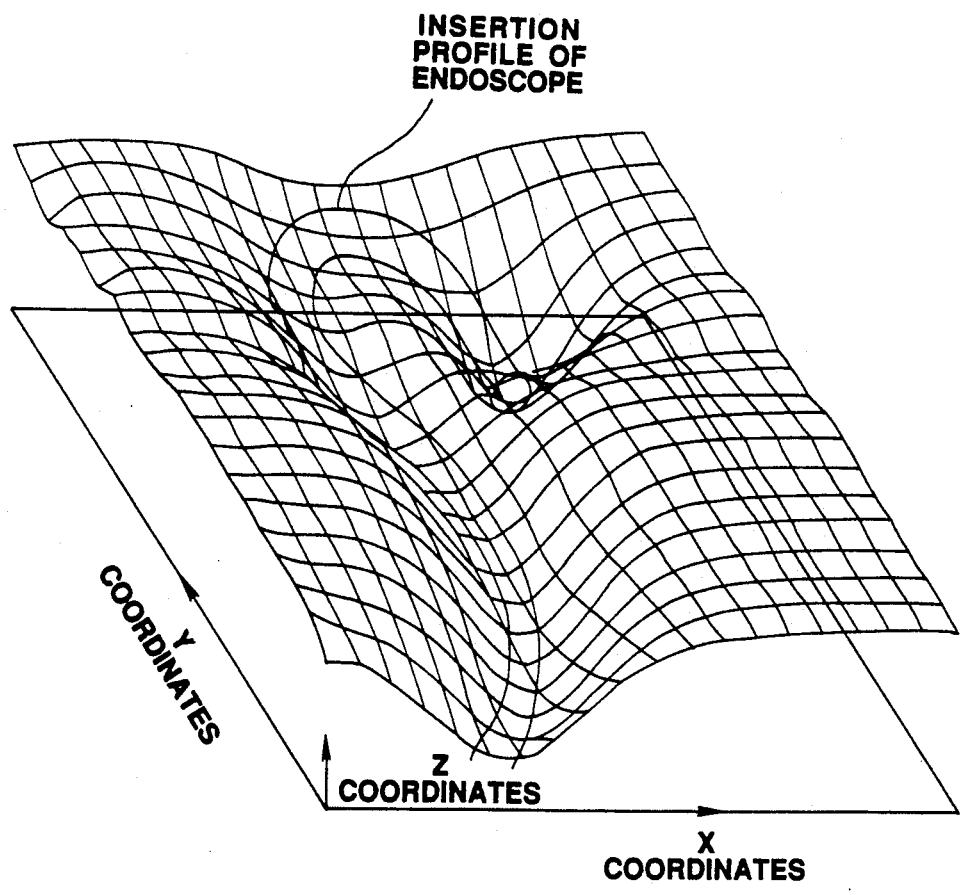

Therefore, when no insertion unit 48a exists in the vicinity of the pickup coil 41, the smoothed feedback voltage E1 equals the standard voltage E0, thus zeroing the output of the differential amplifier IC1. When an insertion unit 48a exists in the vicinity of the pickup coil 41, the difference between the smoothed feedback voltage E2 and the standard voltage E0 is output to the amplifier 44. The computer 45, receiving differential signals (E1-E2) of the voltage from the amplifier 44 as a pickup signal, analyzes and processes the image, and the monitor 46 displays the position and orientation of the insertion unit 48a of the endoscope, as shown in FIG. 8.

The pickup coil 41 is exemplified by solenoid coil with no core, solenoid coil with core, and coil formed on a PC board as shown in FIG. 6 (a), (b), and (c), but not limited to the examples since the shape and material can be altered as required.

Figure 9:
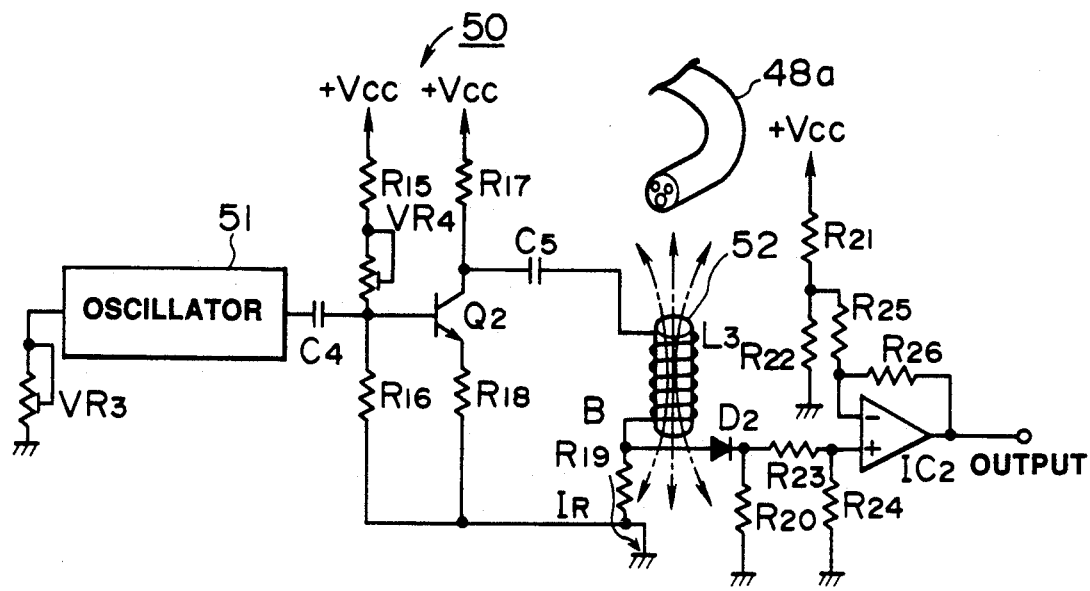
FIG. 9 is an oscillator and pickup circuit diagram showing deformation examples of the oscillator circuit.

FIG. 9 shows the oscillator and detection circuit with construction differing from that of the oscillator circuit 43. The oscillator and detection circuit 50, unlike the self-exciting oscillator circuit 43, is equipped with an external oscillator 51 to detect the position of the endoscope by series resonance. The oscillator and detection circuit comprises an oscillator 51 varying the oscillation frequency with a variable resistor VR3; an amplifier circuit amplifying the output of the oscillator 51; a detection circuit receiving alternating signals amplified by the amplifier circuit and sensing the insertion unit 48a of the endoscope with a change in voltage; a smoothing circuit smoothing the detection signals from the detection circuit; and a differential amplifier circuit outputting smoothed detection signals.

The amplifier circuit comprises a coupling capacitor C4, a variable resistor VR4, and resistors R15 to R18. The detection circuit comprises a series resonant circuit consisting of a resonant capacitor C5 and the coil L3 of the pickup coil 52, and a resistor R19. The differential amplifier circuit comprises resistors R21 and R22 to generate standard voltage E02 by dividing the power supply +VCC, resistors R23 and R24, and a differential amplifier IC2 connecting the power supply +VCC with the power supply −VCC. The standard voltage E02 at the contact of the resistors R21 and R22 is set equivalent to the voltage at the contact (B in the figure) of the coil L3 and the diode D1 without detected object such as the insertion unit 48 of the endoscope. The resonant frequency f02 of the detection circuit is determined by the equation below.

$$f02 = \tfrac{1}{2}\pi(L3 \cdot C5)^{\tfrac{1}{2}} \qquad (2)$$

When the circuit is activated at the resonant frequency f02, series resonance occurs, and the current IR through the resistor R19 becomes maximum with no insertion unit 48a of the endoscope in the vicinity. When an insertion unit 48a exists in the vicinity, the current IR drops. The change is reflected by the voltage change occurring at both ends of the resistor R19, and detected as an output of the differential amplifier IC2.

The circuit 50, unlike the simple oscillation circuit 43, can accept the high-precision oscillator 51, thus stabilizing oscillation frequency. In other respects, it features the same effects as the oscillation circuit 43 in FIG. 2, whose explanation is omitted here.

Figure 10:
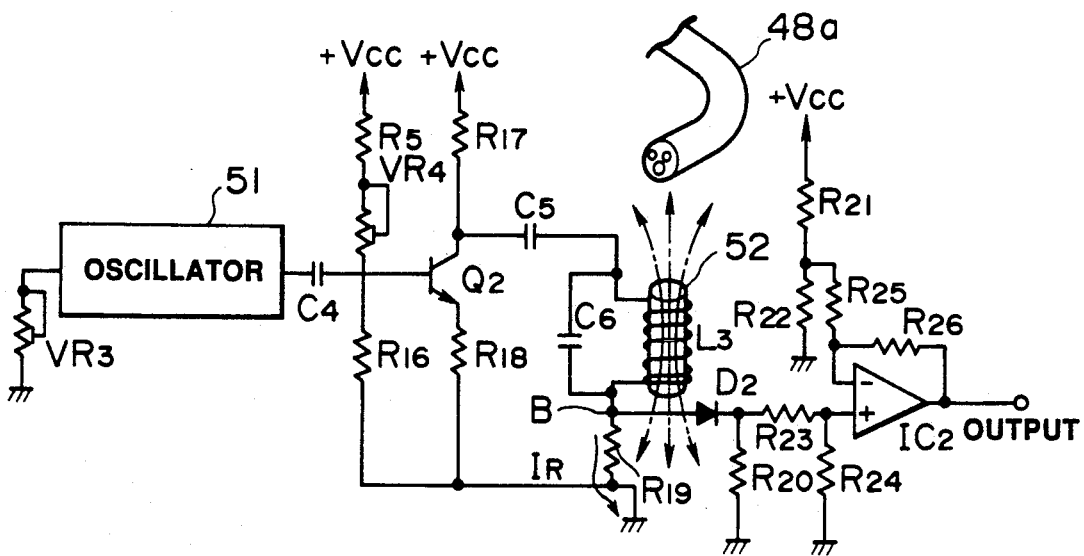
FIG. 10 is an oscillator and pickup circuit diagram showing other deformation examples of the oscillator circuit.

The oscillator and detection circuit 53 shown in FIG. 10, unlike the series resonant circuit of the oscillator and detection circuit 50 in FIG. 9, is equipped with a parallel resonant circuit as a detection circuit. The detection circuit of the oscillator and detection circuit 53 connects a capacitor C6 and the coil L3 of the pickup coil 52 in parallel to detect the position of the insertion unit 48a of the endoscope by detecting the change in current IR caused by parallel resonance as voltage change of the resistor R19. In other respects, it features the same construction and effects as the oscillation and detection circuit 50 in FIG. 9, whose explanation is omitted here.

FIG. 11 shows a second embodiment with construction different from the position and orientation state pickup 40 for endoscope shown in FIG. 1. The position and orientation state pickup 55 for an endoscope is equipped with several pickup coils 41 as magnetic generation means movable in the X direction in the figure and position detection means. The configurations and functions, which are the same as in the position and orientation state pickup 40 for an endoscope, are provided with the same number to omit repetition of explanation.

As shown in FIG. 11, the pickup coils 41 are respectively connected to the oscillator circuit with the oscillator circuits 43, etc. An input selector 57 whose switching is controlled by the computer 45, outputs a detection signal corresponding to a switched pickup coil 41 to the computer 45 via the amplifier 44. The input selector 57 comprises several multiplexers switching the output of the oscillator circuit 56 without displaying; and a logic circuit to select a multiplexer with the switching control signal from the computer 45 without displaying. An analog switch can be used instead of the multiplexer. An interface between the amplifier 44, input selector 57, and the scanner controller 58, and the computer 45 can be activated via an A/D converter, D/A converter or a general-purpose parallel interface GP-IB, etc.

The pickup coils 41 are installed on the Y-direction row shown in FIG. 11 and fixed on a belt 57 installed in the X direction as shown in FIG. 11. A scanner controller 58 controls the pickup coils 41, etc. via a motor 59 driving the belt 57, in the X axis in FIG. 11. The operation of the device is detailed below with the X-axis coordinates in FIG. 11 numbered as x1 to x6 and the coordinates of the pickup coils 41 as y1 to y6.

On the first scanning point, the input selector 57 successively switches the pickup coils 41, etc. located on the coordinates y1 to y6, outputting pickup signals to the amplifier 44. The computer 45 converts the pickup signals from the amplifier 45 by A/D conversion, and successively store them in the specified memory by designating the address. The computer 45 gives an instruction to move the scanning position to the coordinate x2 to the scanner controller 58 and repeats the same procedures at the scanning position x2. The computer 45 analyzes and processes all the obtained detection signals, and the monitor 46 displays the position and orientation state of the insertion unit 48a of the endoscope.

The insertion-state pickup 55 for endoscope features shorter scanning time than the device 40 in FIG. 1, which moves a single pickup coil 41 for scanning, thus accelerating position detection speed. In other respects, it features the same construction and effects as the position and orientation pickup 40 for endoscope in FIG. 1, whose explanation is omitted here.

Figure 12:
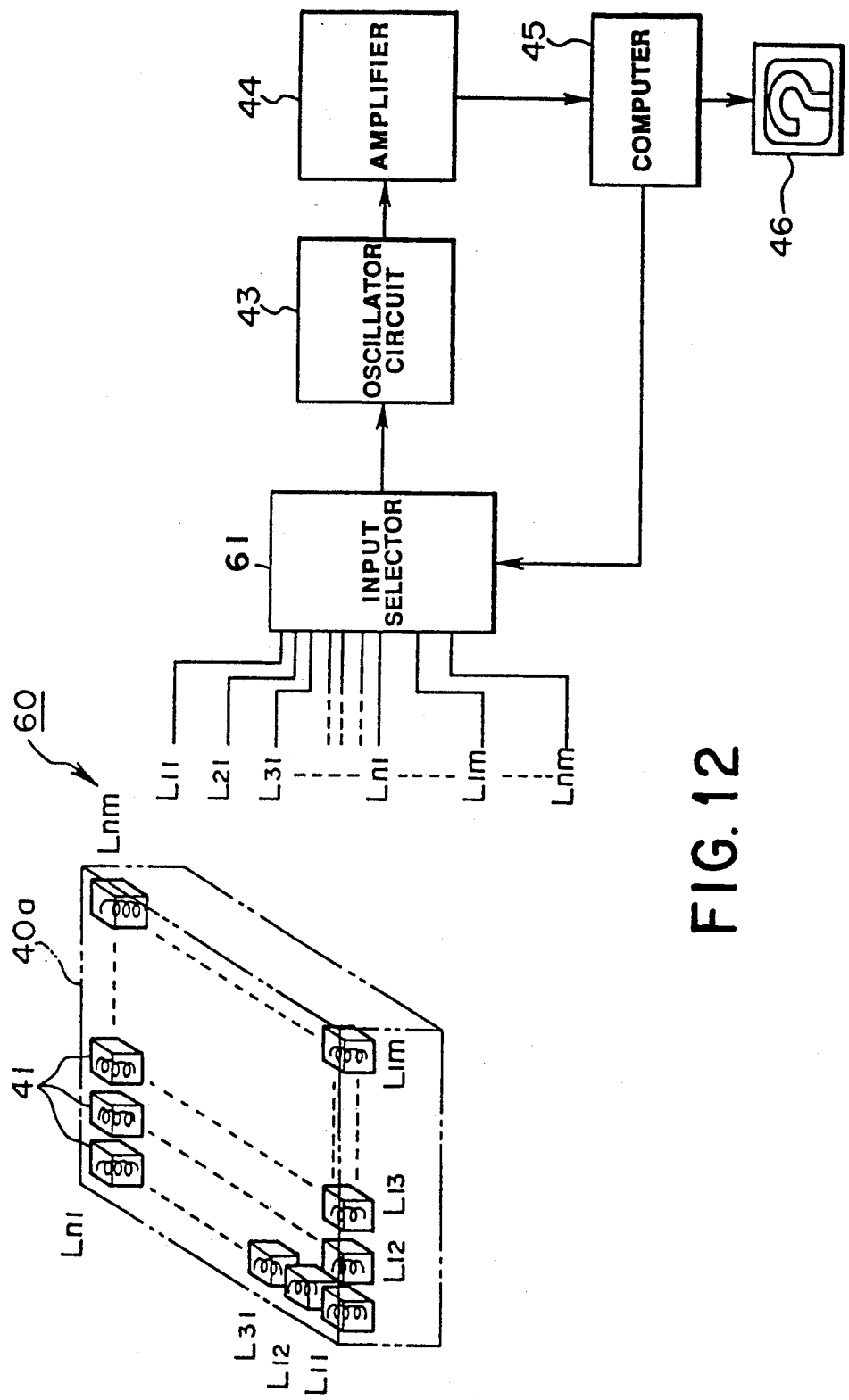
FIG. 12 is a schematic diagram of the insertion-state pickup for the endoscope relating to the third embodiment of the present invention.

FIG. 12 shows the third embodiment with construction different from the position and orientation state pickup 55 for endoscope shown in FIG. 11. The position and orientation state pickup 60 for an endoscope is equipped with several pickup coils 41 covering allover the bed 40a. The configurations and functions the same as in the position and orientation state pickups 40 and 55 for endoscope in FIGS. 10 and 11 are provided with the same number to omit repetition of explanation.

The pickup coils 41 are numbered as L11 to Lnm according to the X and Y coordinates. The input selector 61, according to switching of the computer 46, outputs a detection signal corresponding to the switched pickup coil Lnm to the oscillator circuit 43.

In this construction, the computer 46 connects the oscillator circuit 43 and the pickup coil L11 via the input selector 61, and the oscillator circuit 43 outputs a pickup signal to the computer 45 via the amplifier 44. The pickup coils L12 to Lnm are successively switched in the same manner, and the computer 46 stores all the pickup signals in the internal memory.

The position and orientation state pickup 60 for an endoscope further shortens the scanning time compared with the device 55 in FIG. 11, further accelerating the detection speed for insertion-state detection. The input selector and the oscillator circuit can be exchanged to construct the device shown in FIG. 11. In other respects, it features the same construction and effects as the insertion-state pickups 40 and 55 for endoscope in FIGS. 1 and 11, whose explanation is omitted here.

Figure 13:
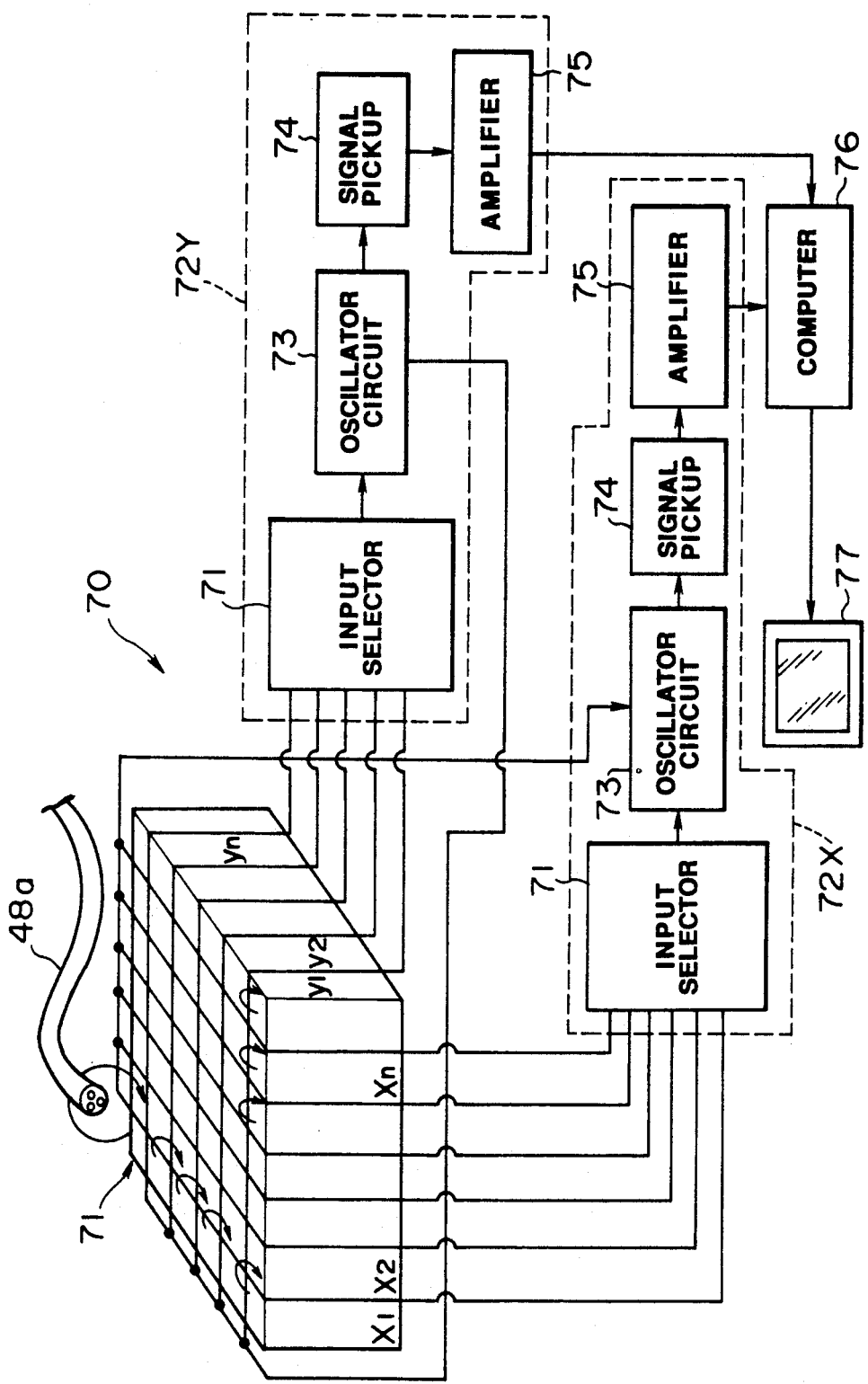
FIG. 13 is a schematic diagram of the insertion-state pickup for the endoscope relating to the fourth embodiment of the present invention.

FIG. 13 shows the fourth embodiment with construction different from the insertion-state pickup 60 for endoscope shown in FIG. 12. The insertion-state pickup 70 for an endoscope is equipped with a bed 70 with grid lines x1 to xn in the X axis and y1 to yn in the Y axis instead of the pickup coils L11 to Lnm. The position and orientation state pickup 70 for endoscope is designed to detect the position and orientation of an endoscope with interaction caused by electro-magnetic induction between the magnetic field around the grid lines x1 to xn and y1 to yn and the insertion unit 48a of the endoscope. The measurement principle is basically identical to that of the device 40 in FIG. 1.

As shown in FIG. 13, the X-axis pickup 72X of the insertion-state pickup 60 for an endoscope comprises an oscillator circuit 73 oscillating high-frequency alternating signals, an input selector 71 switching grid lines x1 to xn and applying an oscillating signal of the oscillator circuit 73, an signal pickup to detect a current or voltage change in the oscillator circuit 73, and an amplifier 75 amplifying output signals from the signal pickup 74. The Y-axis pickup 72Y has the same construction as the X-axis pickup 72X.

The computer 76 stores pickup signals from the X-and Y-axis pickups 72X and 72Y, and analyzes and processes the signals, and the monitor 77 displays the position and insertion state of the insertion unit 48a of the endoscope.

In this construction, the computer 76 switches the input selector 71 via the control line without displaying, and the input selector 71 selects the grid line x1, thus generating the magnetic field around the grid line x1. When an insertion unit 48a of the endoscope exists in the vicinity, the computer 76 stores pickup signals with lower values than when no insertion unit 48a of the endoscope exists. Successively switching the grid lines x2 to xn and y1 to yn, the computer 76 stores respective pickup signals.

If the grid lines x2 and y1 show low-value pickup signals, the computer 76 detects when the insertion unit 48a of the endoscope exists on the intersection of the grid lines. The computer 76 then stores the pickup signals in the memory, and analyzes and processes the signals, and the monitor 77 displays the position and insertion state of the insertion unit of the endoscope.

The insertion-state pickup 70 for an endoscope, incorporating no mechanical scanner, enables high-speed detection. The configurations and functions the same as in the insertion-state pickup 55 shown in FIG. 11 for an endoscope are provided with the same number to omit repetition of explanation.

The figure shows X-Y installation of the grid lines, while X-Z or Y-Z installation is also possible.

FIGS. 14 to 20 relate to the fifth embodiment of the present invention.

Figure 14:
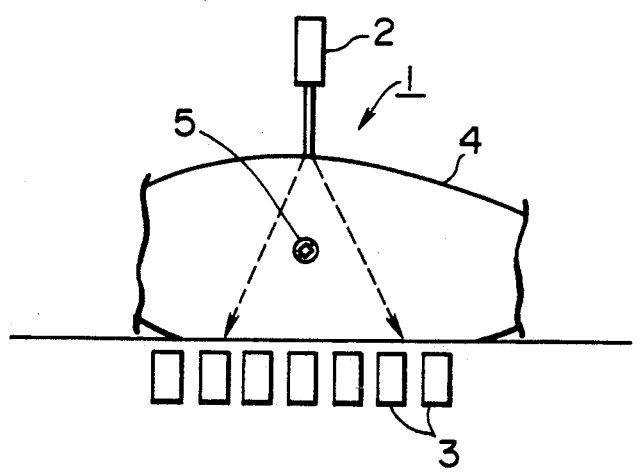
FIGS. 14 to 20 relate to the fifth embodiment of the present invention.
Figure 15:
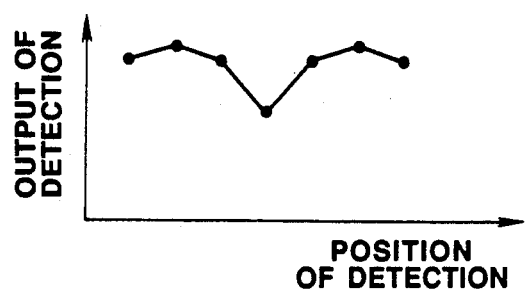

FIG. 14 shows principle construction of the position and orientation state pickup for an endoscope. The position and orientation state pickup 1 for an endoscope comprises a light-emitting means 2 and several light detection means 3. Endoscope 5 is inserted into the tested body 4. While near infrared light (650 nm to 1200 nm) easily penetrates through the organism, the endoscope 5 does not permeate near infrared light. Therefore the position and orientation state pickup 1 for an endoscope employs an infrared light source emitting near infrared light as a light-emitting means. As shown in FIG. 15, the position and orientation state pickup 1 for an endoscope using infrared light shows low intensity of light detected by the light detection means 3 facing the endoscope 5 and high intensity of light penetrating only through the tested body 4. The pickup processes output signals detected by the light detection means 3 to detect the position and orientation state of the endoscope 5 inserted into the tested body 4.

Figure 16:
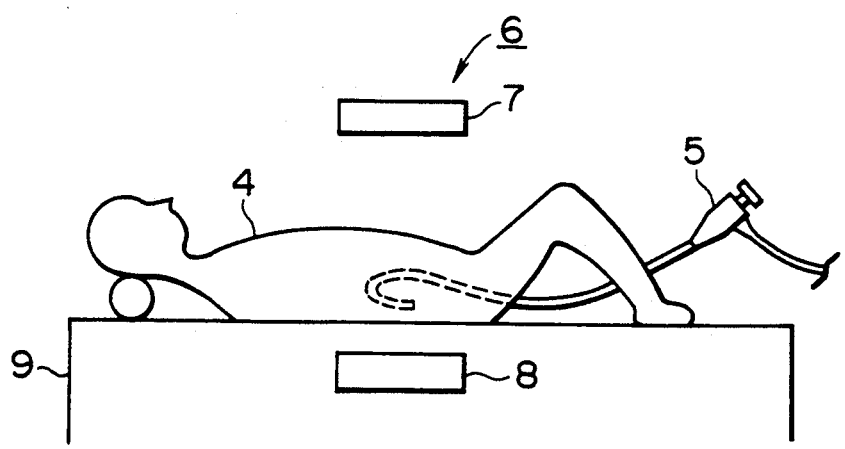
Figure 17:
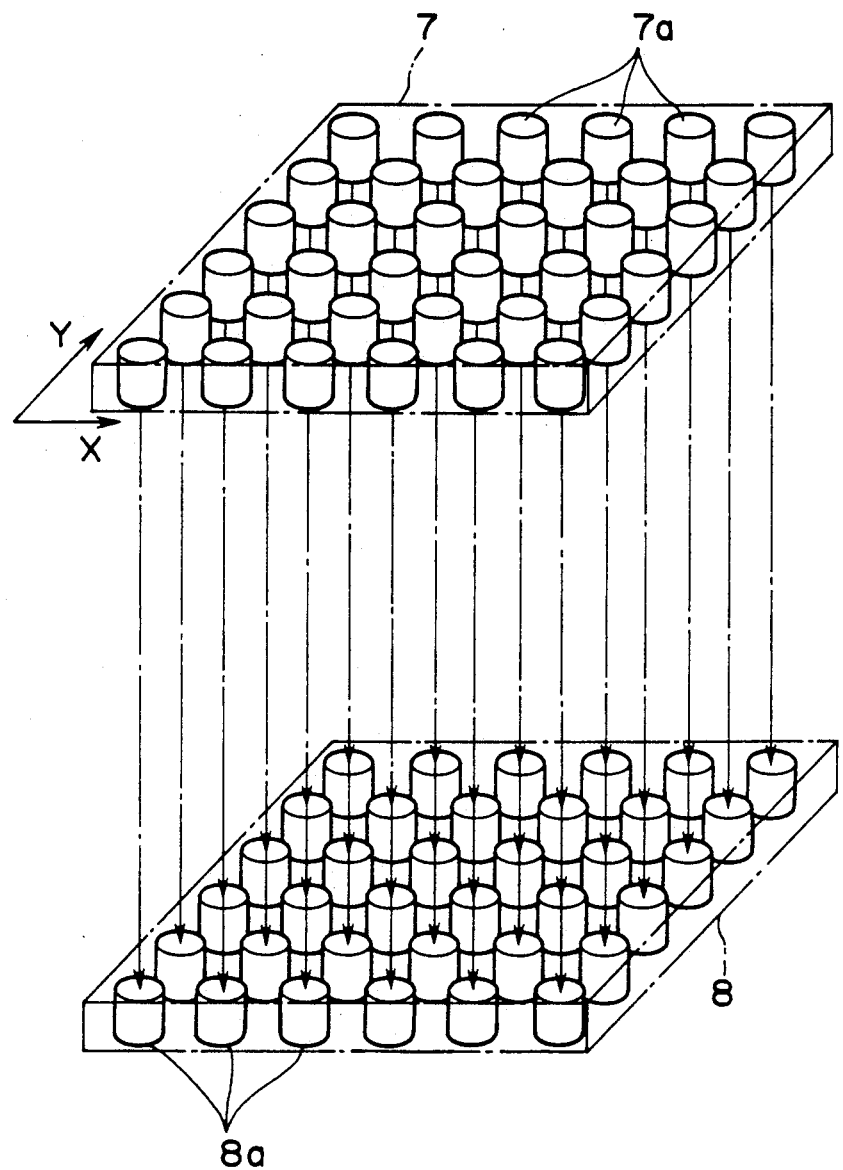
Figure 18:
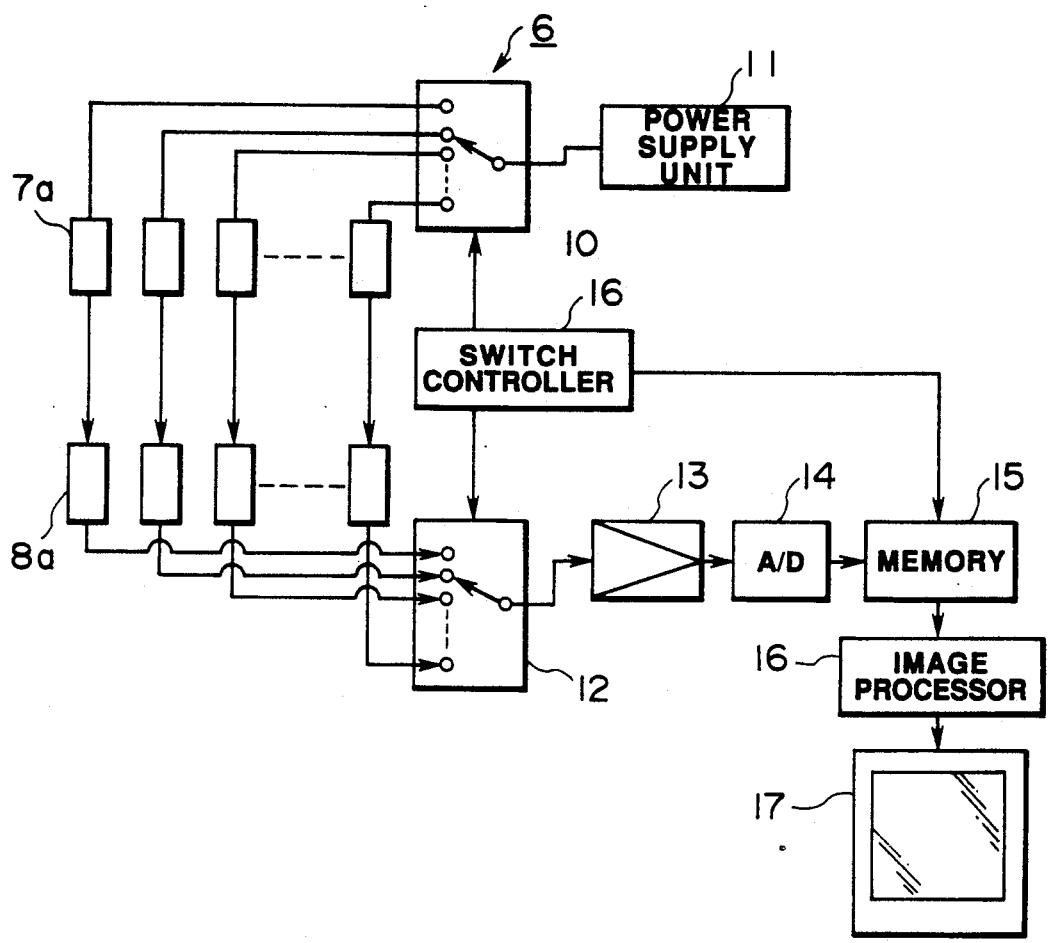

FIGS. 16 to 18 show actual construction of the position and orientation state pickup for endoscope. The position and orientation state pickup 6 for an endoscope, as shown in FIG. 16, has a light source 7 directly facing a pickup 8. As shown in FIG. 17, the light source 7 is equipped with several infrared light sources 7a, etc., as a light-emitting means while the pickup 8 is equipped with several infrared light pickups 8a, etc. The infrared light sources upwards from 7a are respectively paired with the infrared light pickups upwards from 8a on, detecting the position orientation of the endoscope 5 inserted into the body 4 laid on the bed 9. A light source with spectral characteristics in the infrared range such as xenon, halogen, or laser light source is used for the infrared light source 7a. A semi-conductor light-receiving element such as a silicone photo-diode or photoelectric multiplier is used for the pickup 8a. A diaphragm and lens not shown in the figure are used in the infrared light sources and the pickups to make a light beam thin, ensuring directivity, and enhancing detection sensitivity.

FIG. 18 is a schematic diagram of the position and orientation state pickup 6 for an endoscope. The infrared light sources upwards from 7a are connected to the power supply unit 11 via the power switch 10. The infrared light pickups upwards from 8a are connected to an amplifier 13, an A/D (analog/digital) converter 14, and a memory 15 via a pickup output switch 12.

The power switch 10, pickup output switch 12, and memory 15 are controlled by a switch controller 16 for their switching and timing. The amplifier 13 amplifies pickup signals of the infrared light pickup 8 via the pickup output switch 12, and the A/D converter 14 converts the amplified pickup signals from analog-to-digital mode to obtain pickup data. The memory 15 stores pickup data corresponding to the infrared light pickup 8 into the address selected with the switch controller 16. The image processor 16 processes pickup data in the memory 15 and converts them to standard image signals 2. The monitor 17 displays the position and insertion state of the endoscope 5.

Figure 19:
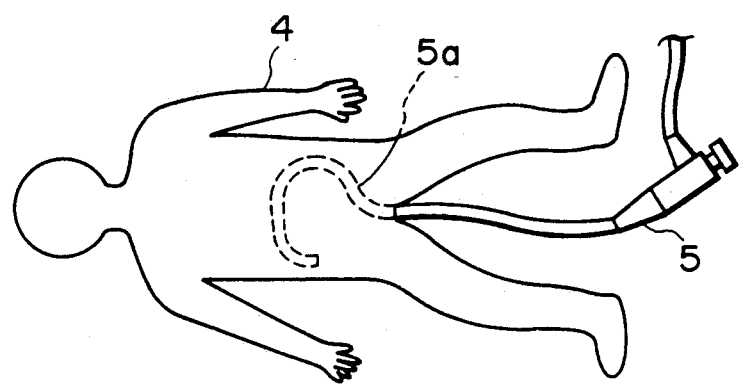

The operation of the position and orientation state pickup 6 for an endoscope is explained below. As shown in FIG. 19, the insertion unit 5a of the endoscope 5 is inserted into the body to be tested 4, when laid on the bed 9.

The switch controller 16 trips the power switch 10 to supply the power to an infrared light source 7a shown in FIG. 17 (the left light source, for example) from the power unit. The switch controller 16 simultaneously trips the pickup output switch 12 to select a infrared light pickup 8a facing the selected infrared light source 7a. The selected infrared light pickup 8a outputs a pickup signal to the amplifier 13. Receiving a pickup signal from the amplifier 13, the A/D converter 14 outputs the pickup data to the memory 15, which stores the pickup data in the address designated by the switch controller 16.

Figure 20:
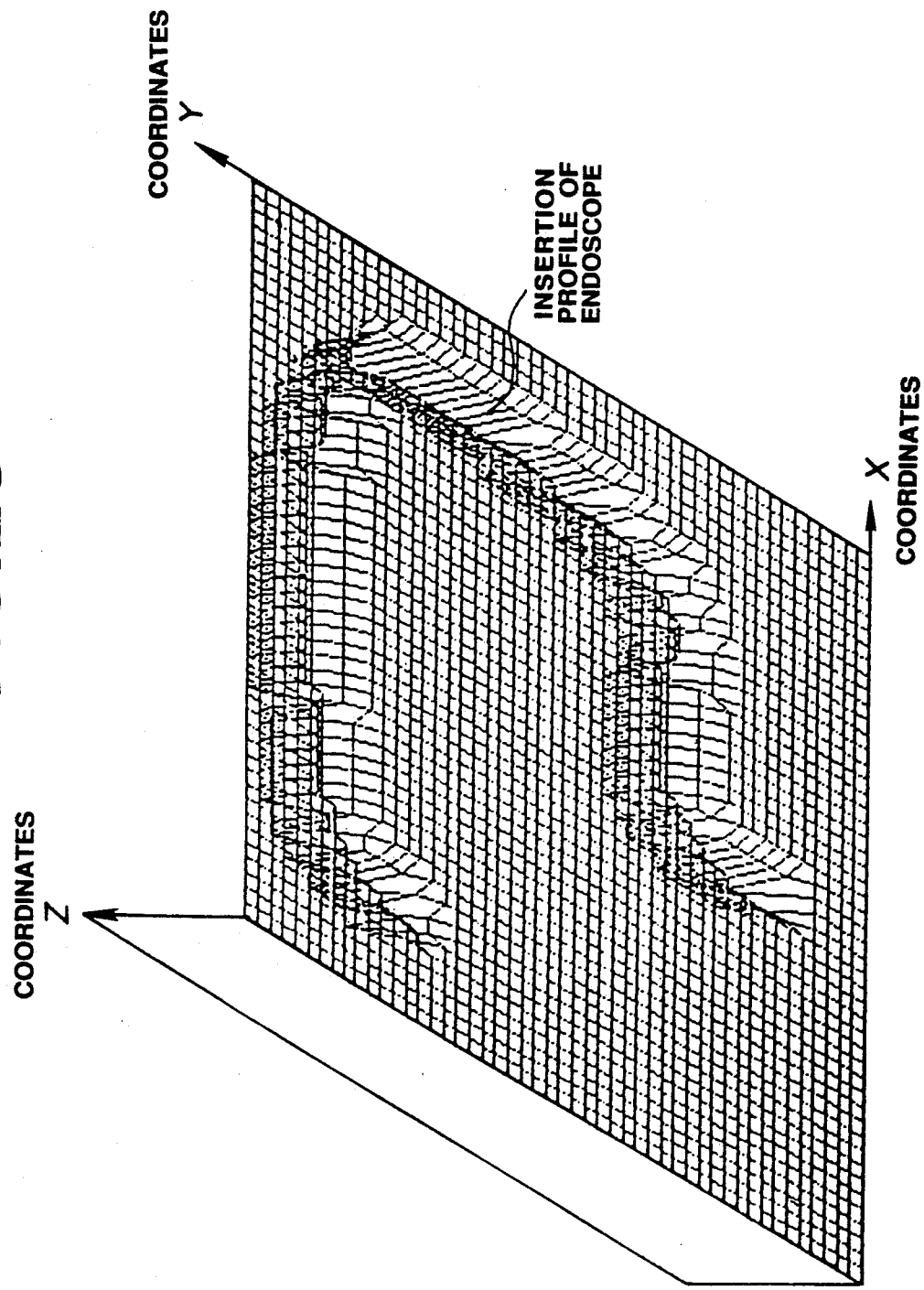

The switch controller 16 trips the power switch 10 to supply power to a infrared light source 7a next to the first-selected infrared light source 7a (in the X axis in the figure) from the power unit 11. The switch controller 16 switches the pickup output switch 12 and the address of the memory 15, which stores the pickup data in the next address. The switch controller 16 electrically scans irradiating lights from the infrared light source 7a, and the image processor 16 converts all the pickup data to the standard image signals with all the pickup data stored in the memory. The monitor 17 displays the position and insertion state of the endoscope as shown in FIG. 20. The X and Y axes shown in FIG. 20 show coordinates corresponding to the infrared light sources from 7a on and the infrared light pickups from 8a on as in FIG. 17. The Z axis, showing intensity of light detected by the infrared light pickups, is displayed as light excessively shielded by the endoscope 5.

In this embodiment, the infrared light sources and infrared light pickups are electrically scanned, outputting pickup data at high-speed and thus accelerating detection by the position and orientation state pickup for endoscope.

Figure 21:
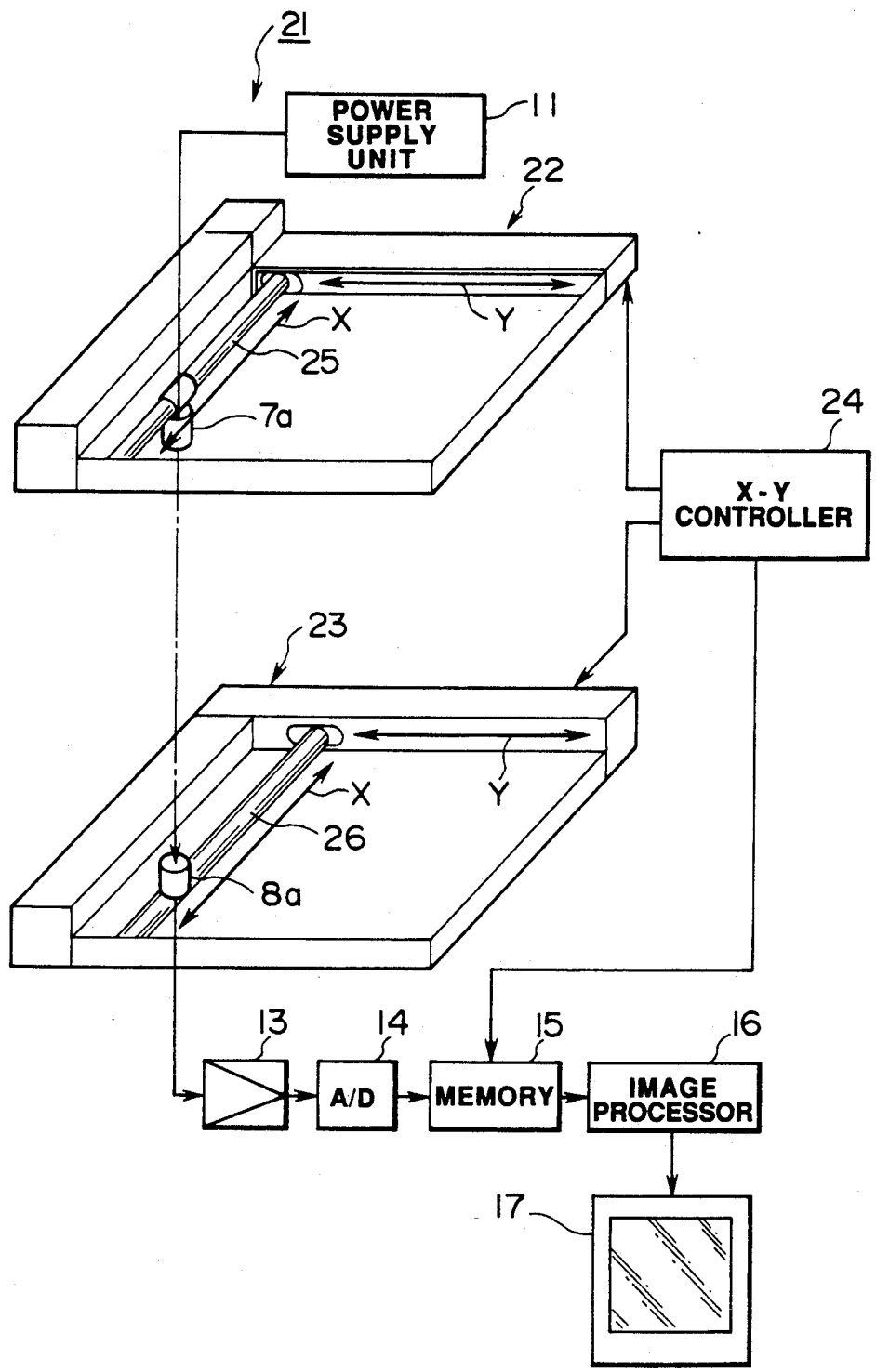
FIG. 21 is a schematic diagram of the insertion-state pickup for the endoscope relating to the sixth embodiment of the present invention.

FIG. 21 is a schematic diagram of the position and orientation state pickup for endoscope relating to the sixth embodiment of the present invention. The position and orientation state pickup 21 for endoscope is equipped with a light source unit X-Y stage 22 and a pickup X-Y stage 23 respectively with a single light-emitting means and light pickup means instead of the light sources 7 and pickups 8 as shown in the fifth embodiment. The light-emitting means, the infrared light source 7a and the light pickup means, the infrared pickup 8a face each other to align their light axes and scan objects in two dimension. In this embodiment, the device is equipped with an X-Y controller 24 instead of the switch controller 16. The configurations and functions the same as in the fifth embodiment are provided with the same number to omit repetition of explanation.

The X-Y controller 24 drives and controls the light source X-Y stage 22 and the pickup X-Y stage, and switch the address of the memory 13. The light source X-Y stage 22 is equipped with the infrared light source 7a movable in the X axis on the shaft 25 movable in Y axis. The pickup X-Y stage 23 is equipped with the infrared pickup 8a movable in the X axis on the shaft 26 movable in Y axis.

In this construction, the X-Y controller 24 drives the light source X-Y stage 22 and scans the infrared light source 7a attached on the shaft 25. The X-Y controller 24 scans the infrared pickup 8a on the shaft 26 of the pickup X-Y stage 23 to face it to the light source 7a. The infrared pickup 8a outputs pickup signals to the memory 15 via the A/D converter as pickup data. The memory 15, according to instructions from the X-Y controller 24, stores pickup data entered by scanning. The monitor 17, receiving output signals from the image processor 16, displays the position and orientation state of the endoscope 5.

Figure 22:
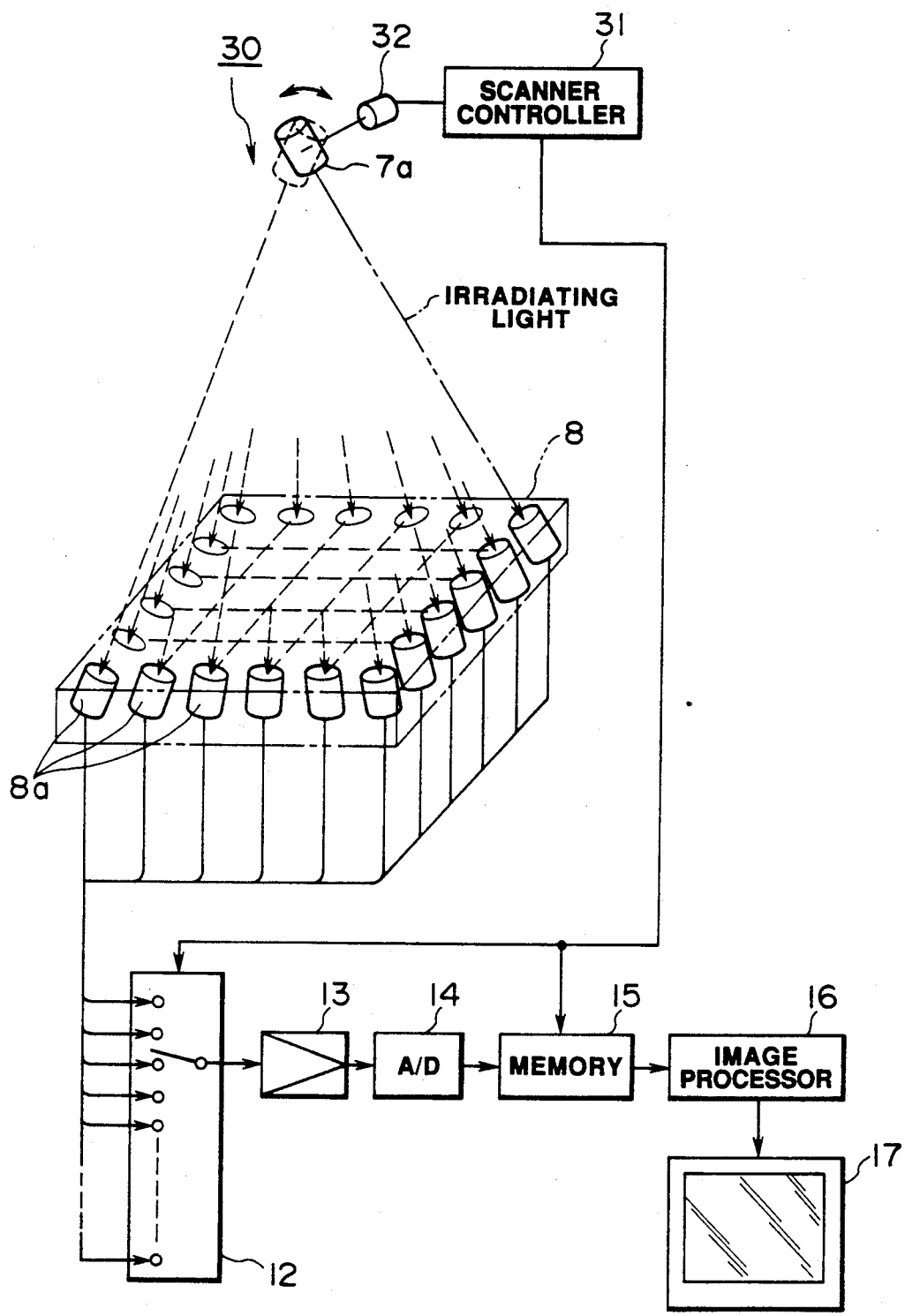
FIGS. 22 and 23 relate to the seventh embodiment of the present invention.
Figure 23:
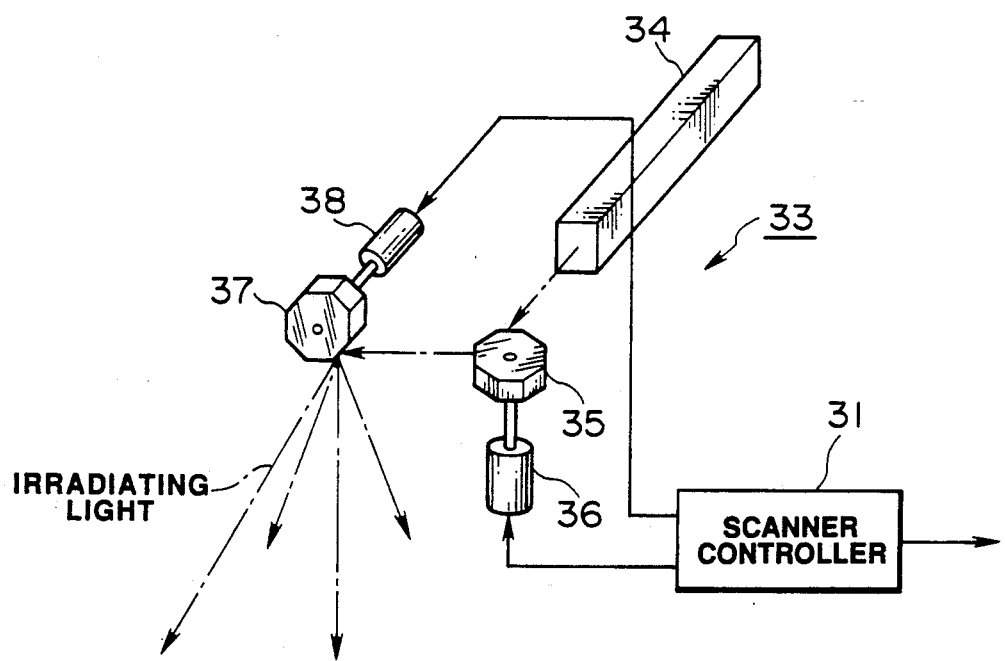

FIGS. 22 and 23 relates the seventh embodiment of the present invention.

This embodiment, unlike the fifth embodiment, is equipped with a single light-emitting means and several light pickup means. A single light-emitting means, an infrared light source 7a, rotating and being scanned successively, irradiates light to the light pickups one by one. The device in this embodiment is equipped with a scanner controller 31 instead of the switch controller 16. The configurations and functions same as in the fifth embodiment are provided with the same number to omit repetition of explanation.

As shown in FIG. 22, the position and orientation state pickup 30 for an endoscope is equipped with a motor 32 rotated and controlled by the scanner controller 31. The rotating infrared light source 7a is installed facing several infrared pickups 8a. The scanner controller 31 controls switching of the pickup switch 12 and the address of the memory 15.

FIG. 23 shows the embodiment of a means to control radiating light in the position and orientation state pickup for an endoscope.

As shown in FIG. 23, the scanner light source 33 is equipped with a laser source 34 as a light-emitting means to irradiate near infrared laser beams, a first rotary polygon mirror 35 to reflect laser beam from the laser source 34, a first motor 36 to rate the first rotary polygon mirror 35, a second rotary polygon mirror 37 further reflecting laser beam from the laser source 34 reflected by the first rotary polygon mirror 35 and a second motor 38 to rotate the second rotary polygon mirror 37. The scanner controller 31 drives and controls rotation of the first and second motors 35 and 38.

In this construction, the laser source 34 emits laser beams and is controlled by the scanner controller. The first and second motors 36 and 38 rotates the first and second rotary polygon mirrors 35 and 37 to radiate a laser beam to a single light pickup 8a. The laser beam is successively scanned by controlling the rotation angle of the first and second rotary polygon mirrors 35 and 37. The memory 15 stores pickup data from all the infrared pickups 8a. The configurations and functions same as in the fifth embodiment are provided with the same number to omit repetition of explanation.

In this embodiment, scanning by controlling the rotation angle of the rotary polygon mirrors 35 and 37 enhances the scanning resolutions and ensures accuracy. It is also effective in ensuring high detection accuracy with the number of the infrared light pickups 8a increased.

The known ultrasonic deflecting system other than the rotary polygon mirror can also be used for scanning of the laser beam 34.

Figure 26:
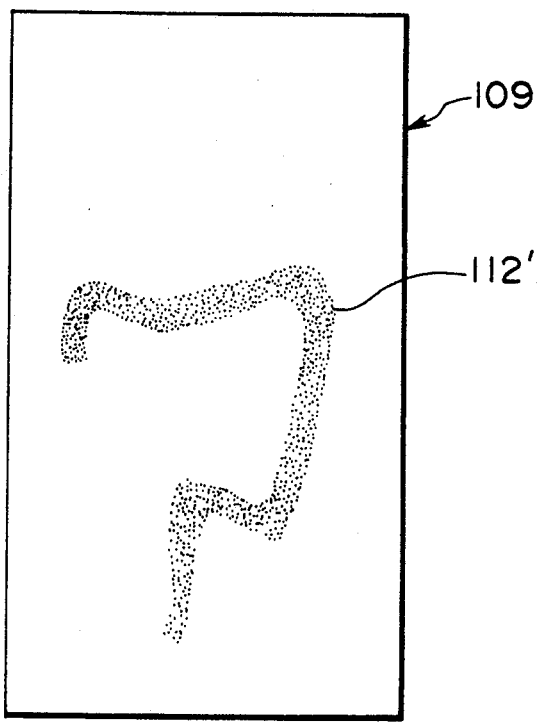

FIGS. 24 to 26 relates to the eighth embodiment of the present invention.

The position and orientated state pickup for endoscope, as shown in FIG. 24, comprises an endoscope 102 with a fiber scope, a light source 103 to supply light to the endoscope 102, an externally-installed TV camera for endoscope (hereinafter referred to as a TV camera) 104, which is connected to the eye-piece mentioned below of the endoscope 102 and monitors the image taken by the endoscope, a camera control unit (hereinafter referred to as a CCU) 105 processing signals from the TV camera 104, a monitor 106 displaying image signals output by the CCU 105, a bed 108 on which a patient 107 is lying, a magnetic detection means 109 installed at the bottom of the bed 108, a magnetic field monitoring system 110, which is installed below the bed 108, generates magnetic force, and monitors the magnetic detection means 109, and a controller 111 connected with the magnetic field monitoring system 110.

The endoscope 102 comprises a flexible, thin insertion unit 112, a large-diameter controller 113 connected to the base of the insertion unit 112, an eyepiece 114 attached at the end of the controller 113d, a light guide cable 115 extended from the side of the controller 115, and a connector equipped at the end of the light guide cable 115.

The insertion unit 112 is ferromagnetic.

The insertion unit 112 and the controller 113 of the endoscope 102 are equipped with a built-in image guide to transmit the monitored image. The image guide 127 has an end installed on the image-formation plane of the object optical system attached on the tip of the insertion unit 112 and the other end facing the eyepiece optical system attached on the eyepiece 119.

The TV camera 104 comprises a camera unit 117 detachable to the eyepiece 114, a universal cord 118 extended from the rear end of the camera unit 117, and a connector 119 equipped at the end of the universal cord 118.

The TV camera 117 is equipped with an image-pickup optical system 121 facing the eyepiece optical system 120, and the image-formation plane of the fixed image-pickup elements such as a charge coupled device (hereinafter referred to as a CCD) 122 at the image-formation position of the image-pickup optical system 121.

The CCD 122 is connected with a signal line 123, which is built in the universal cord 118 and connected to the CCU with the connector 119.

The light source 103 has a built-in lamp 125 to supply radiating light to the endoscope 102, and the light from a lamp 125 is supplied to the incident plane of the light guide (not appearing in the figure) with the aid of a capacitor lens 126.

The light is transmitted by the light guide, and radiates the object image (not appearing in the figure) through the outgoing plane of the light guide equipped on the insertion unit 112.

As mentioned earlier, the lighted object image is focused on the incident plane of the image guide 127 by the object optical system (not appearing in the figure) installed on the tip of the insertion unit 102, transmitted to the outgoing plane of the image guide 127, and can be observed by observing the eyepiece optical system 120 with naked eyes. The object image observed by the eyepiece optical system 120 can be focused on the photo-electric conversion plane of the CCD 122 by using the image-pickup optical system 121 of the TV camera 104.

The object image formed on the photo-electric conversion plane of the CCD 122 is converted into electric signals with the CCD 122, entered to the CCU 105, and displayed by the monitor after signal processings.

The magnetic-field observation means 110 is connected to the controller 111 via a cable 124.

The controller 111 generates a uniform magnetic field for the magnetic-field observation means 110 and displays a change in the magnetic field detected by the magnetic detection means 109 on the monitor 106.

The magnetic-field observation means 110 has a construction sealing magnetic fluid 131 in glass plates 130, as shown in FIG. 25.

The magnetic fluid 131 fluctuates the density of the magnetic substances in the fluid depending on the intensity of the magnetic field. The density fluctuation changes the reflectance of the light.

The function of the thus-constructed position and orientation state pickup for endoscope is explained below.

Before the insertion unit 112 of the endoscope 102 is inserted into the body cavity of the patient 107, the magnetic-field detection means 109 creates a uniform magnetic field for the magnetic-field observation means 110 under control by the controller 111.

Thus the density of the magnetic fluid 131 sealed in the glass 130 of the magnetic-field detection means becomes uniform, ensuring uniform reflection of light.

When the insertion unit 112 of the endoscope 102 is inserted into the body cavity of the patient 107, the density of the magnetic fluid 131 sealed in the glass 130 fluctuates according to the magnetic force of the insertion unit 112.

The density of the magnetic fluid 131 sealed in the glass 130 of the magnetic-field detection means 109 fluctuates as the magnetic fluid concentrates in the shape of the insertion unit 112 as shown in FIG. 26.

The magnetic-field observation means 110 monitors a density change of the magnetic fluid 131 sealed in the glass 130 of the magnetic-field detection means 109 and outputs to the controller 111.

The controller 111, as mentioned earlier, displays the state of the magnetic-field detection means 109 monitored by the magnetic-field observation means 110, for example, on the monitor 106.

In short, detection of the insertion state of the endoscope by utilizing a change in magnetic force is ensured.

Figure 27:
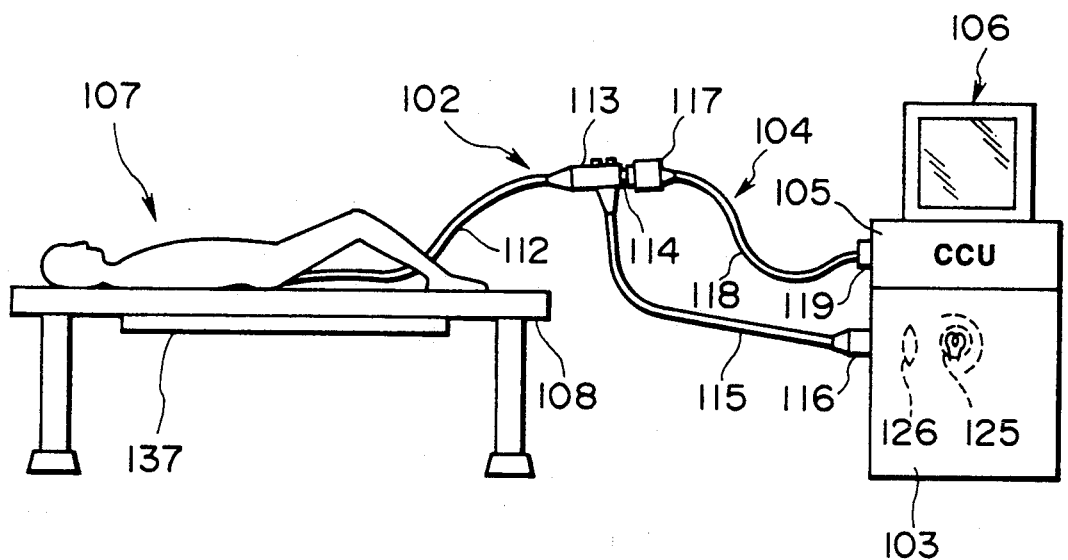
FIGS. 27 and 28 relate to the ninth embodiment of the present invention.
Figure 28:
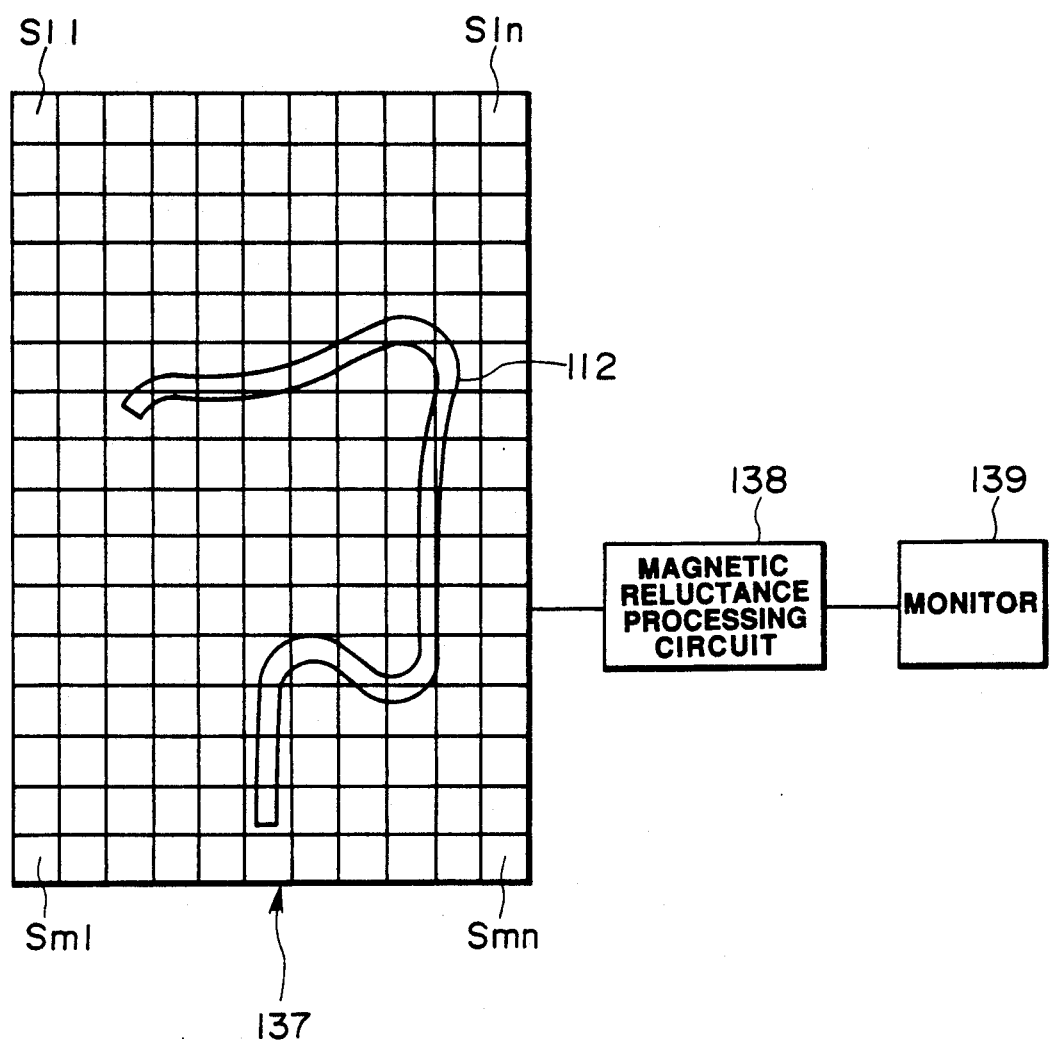

FIGS. 27 and 28 relates to the ninth embodiment of the present invention.

Configuration and functions the same as in the eighth embodiment are provided with the same number to omit repetition of explanation.

The position and orientation state pickup for endoscope, as shown in FIGS. 27 and 28, comprises an endoscope 102, a light source 103, a TV camera 104, a CCU 105, a monitor 106, and a bed 108 on which a patient 107 is lying, and is equipped with a magnetic resistance element matrix plate resistance processing circuit 138 to detect the position and orientation state with processing circuit 138 to detect the position and orientation state with the magnetic resistance elements S11 to Smn on the matrix plate in a matrix pattern, and a indicator 139 to show image signals from the magnetic resistance processing circuit 138.

The magnetic resistance processing circuit 138 has its input terminals connected with the magnetic resistance elements S11 to Smn, respectively, and its output terminals with the indicator 139.

The function of this position and orientation state pickup for endoscope is explained below.

The magnetic resistance elements S11 to Smn attached on the matrix plate 137 fluctuates its resistance depending on the magnetic force from the insertion unit of the endoscope.

With the resistance fluctuation, the magnetic resistance processing circuit 138 obtains the position of the insertion unit on the matrix plate and outputs it to the indicator in the form of the image signal.

An LED matrix arranged as the magnetic resistance elements S11 to Smn may be used for the indicator 139 and driven to cause luminance fluctuation according to the resistance of the magnetic resistance elements S11 to Smn.

In short, the device detects the magnetic field by electric processing and displays the intensity of the magnetic field by responding to the intensity.

Configurations and functions the same as in the eighth embodiment are provided with the same number to omit repetition of explanation.

The insertion state of the insertion unit may b displayed in three dimensions according to the intensity of the magnetic field detected from the insertion unit of the endoscope.

In this invention, it is apparent that working modes different in a wide range can be formed on the basis of this invention without departing from the spirit and scope of the invention. This invention is not restricted by any specific embodiment except being limited by the appended claims.

What is claimed is:

1. A position and orientation state pickup for detecting the position and orientation state of an endoscope inserted in a living body comprising:

a means for forming an electromagnetic field in the living body from outside said living body having a frequency below the visible range, wherein said means for forming an electromagnetic field is a means for generating an alternating magnetic field, including a coiling means for emitting a magnetic field toward a living body and an oscillator circuit for supplying alternating current to the coiling means; and detecting means for determining the position and orientation of said endoscope from the detection of the energy distribution in said electromagnetic field influenced by the endoscope in said living body.

2. A position and orientation state pickup according to claim 1 wherein said means for forming an electromagnetic field forms electro-magnetic energy in the form of a static energy field.

3. A position and orientation state pickup according to claim 2 wherein said electromagnetic-field generating means is a magnetic-filed generating means for emitting said static magnetic field.

4. A position and orientation state pickup according to claim 3 wherein said magnetic-field generating means generates a uniform magnetic field in the living body, and wherein said detecting means is positioned between said magnetic-field generating means and said living body.

5. A position and orientation state pickup according to claim 1 wherein said detecting means comprises a plurality of magnetic resistance elements arranged in a matrix pattern.

6. A position and orientation state pickup according to claim 5 wherein said position and orientation state pickup includes a means for processing signals from said plurality of magnetic resistance elements and a means for displaying a position and orientation state of the endoscope.

7. A position and orientation state pickup for detecting the position and orientation state of an endoscope inserted in a living body comprising:

a means for forming an electromagnetic field in the living body from outside said living body having a frequency below the visible range, wherein said means for forming an electromagnetic field is a means for generating an alternating magnetic field, including a coiling means for emitting a magnetic field toward a living body and an oscillator circuit for supplying alternating current to the coiling means, and wherein said coiling means includes a plurality of linearly arranged coils and a supporting means to hold the coils to allow the coils to move in both longitudinal and perpendicular directions; and detecting means for determining the position and orientation of said endoscope from the detection of energy distribution in said electromagnetic field influenced by the endoscope in said living body.

8. A position and orientation state pickup according to claim 7, wherein said means for detecting includes a means for detecting a change in the quality factor of said coiling means.

9. A position and orientation state pickup according to claim 8, wherein said change in the quality factor is obtained from a current value or a voltage value fed through said coiling means.

10. A position and orientation state pickup according to claim 9, wherein said coiling means includes a plurality of coils arranged in a matrix pattern.

11. A position and orientation state pickup according to claim 10, wherein said coils are buried and arranged in a bed for a patient.

12. A position and orientation state pickup for detecting the position and orientation state of an endoscope inserted in a living body comprising:

a means for forming an electromagnetic field in the living body from outside said living body having a frequency below the visible range; and a detection means for detecting two-dimensional energy distribution in said electromagnetic field influenced by the endoscope in said living body wherein said means for forming an electromagnetic field is a radiating means for radiating infrared rays.

13. A position and orientation state pickup according to claim 12, wherein said detecting means comprises an infrared ray detecting means established facing said radiating means to cover the body.

14. A position and orientation state pickup according to claim 13, wherein said detecting means comprises a plurality of infrared intensity detectors in a matrix pattern.

15. A position and orientation state pickup according to claim 14, wherein said infrared-ray radiating means comprises a plurality of infrared light sources in a matrix pattern respectively facing said plurality of infrared intensity detectors.

16. A position and orientation state pickup according to claim 13, wherein said infrared-ray radiating means produces infrared radiation movable on a two-dimensional plane, and, wherein said infrared intensity detectors comprise an optical pickup moving with said light source on a two-dimensional plane.

17. A position and orientation state pickup for detecting the position and orientation state of an endoscope inserted in a living body, comprising:

a means for forming an electro-magnetic field in the living body from outside said living body having a frequency below the visible range;

a detection means for detecting two-dimensional energy distribution in said electro-magnetic field influenced by the endoscope in said living body, wherein said detecting means comprises transparent panel members sealing magnetic fluid.

18. A position and orientation state pickup according to claim 17, wherein said detecting means comprises a plurality of magnetic resistance elements arranged in a matrix pattern.

* * * * *